US011300766B2

(12) United States Patent
Ohashi et al.

(10) Patent No.: US 11,300,766 B2
(45) Date of Patent: Apr. 12, 2022

(54) APPARATUS, INFORMATION PROCESSING APPARATUS, PROGRAM, AND INFORMATION PROCESSING METHOD

(71) Applicant: Sony Corporation, Tokyo (JP)

(72) Inventors: Takeshi Ohashi, Kanagawa (JP); Naofumi Matsui, Kanagawa (JP); Suguru Aoki, Tokyo (JP); Tomoya Onuma, Shizuoka (JP)

(73) Assignee: Sony Corporation, Tokyo (JP)

( * ) Notice: Subject to any disclaimer, the term of this patent is extended or adjusted under 35 U.S.C. 154(b) by 659 days.

(21) Appl. No.: 16/307,582

(22) PCT Filed: May 11, 2017

(86) PCT No.: PCT/JP2017/017823
§ 371 (c)(1),
(2) Date: Dec. 6, 2018

(87) PCT Pub. No.: WO2017/217148
PCT Pub. Date: Dec. 21, 2017

(65) Prior Publication Data
US 2019/0212537 A1 Jul. 11, 2019

(30) Foreign Application Priority Data
Jun. 13, 2016 (JP) .............................. JP2016-116772

(51) Int. Cl.
*G02B 21/00* (2006.01)
*C12M 1/34* (2006.01)
(Continued)

(52) U.S. Cl.
CPC .......... *G02B 21/0044* (2013.01); *C12M 1/00* (2013.01); *C12M 1/34* (2013.01); *C12M 1/42* (2013.01);
(Continued)

(58) Field of Classification Search
CPC .. G02B 21/0044; G02B 21/34; G02B 21/365; C12M 41/36; C12M 1/00; C12M 1/34;
(Continued)

(56) References Cited

U.S. PATENT DOCUMENTS 8,605,968 B2 * 12/2013 Alexandrov ......... G06K 9/0014
382/128
2005/0194535 A1 * 9/2005 Noji ........................ H01J 37/28
250/311
(Continued)

FOREIGN PATENT DOCUMENTS

CN 101880626 A 11/2010
CN 101 880 626 B 4/2013
(Continued)

OTHER PUBLICATIONS

International Search Report and Written Opinion and English translation thereof dated Aug. 1, 2017 in connection with International Application No. PCT/JP2017/017823.
(Continued)

*Primary Examiner* — Stephone B Allen
*Assistant Examiner* — Rahman Abdur
(74) *Attorney, Agent, or Firm* — Wolf, Greenfield & Sacks, P.C.

(57) ABSTRACT

An apparatus includes: an accommodation unit capable of accommodating a cell and liquid; and a rotation unit that produces a flow in the liquid in the accommodation unit to rotate the cell. The apparatus further includes a rotation controller unit that detects a rotation amount input from an input device, and controls the flow of the liquid produced by each of the output ports on a basis of the input rotation amount to control a rotation amount of the cell.

15 Claims, 8 Drawing Sheets

(51) Int. Cl.
*C12M 1/00* (2006.01)
*C12M 3/00* (2006.01)
*C12M 1/42* (2006.01)
*G02B 21/34* (2006.01)
*C12M 1/36* (2006.01)
*G06T 7/70* (2017.01)
*G02B 21/36* (2006.01)
*B01L 3/00* (2006.01)

(52) U.S. Cl.
CPC ............. *C12M 3/00* (2013.01); *C12M 21/06* (2013.01); *C12M 41/36* (2013.01); *C12M 41/48* (2013.01); *G02B 21/34* (2013.01); *G02B 21/365* (2013.01); *G06T 7/70* (2017.01); *B01L 3/502761* (2013.01); *G06T 2207/10056* (2013.01); *G06T 2207/30024* (2013.01)

(58) Field of Classification Search
CPC .......... C12M 3/00; C12M 1/42; C12M 21/06; C12M 41/48; G06T 7/70; G06T 2207/10056; G06T 2207/30024; B01L 3/502761
USPC ......................................................... 359/368
See application file for complete search history.

(56) References Cited

U.S. PATENT DOCUMENTS

| | | | | |
|---|---|---|---|---|
| 2006/0005634 | A1* | 1/2006 | Schroeder | B01L 3/50273 73/861 |
| 2011/0092762 | A1* | 4/2011 | Wong | G01N 33/5005 600/34 |
| 2012/0094326 | A1* | 4/2012 | Wong | G06K 9/00147 435/34 |
| 2014/0087412 | A1* | 3/2014 | Fouras | G01N 15/10 435/29 |

FOREIGN PATENT DOCUMENTS

| | | |
|---|---|---|
| CN | 103087898 A | 5/2013 |
| JP | 2010-181402 A | 8/2010 |
| JP | 2011-017620 A | 1/2011 |
| JP | 2013-502233 A | 1/2013 |
| JP | 2013-118848 A | 6/2013 |
| JP | 2013-243968 A | 12/2013 |
| JP | 2014-090692 A | 5/2014 |
| WO | WO 2011/025736 A1 | 3/2011 |
| WO | WO 2012/142664 A1 | 10/2012 |

OTHER PUBLICATIONS

International Preliminary Report on Patentability and English translation thereof dated Dec. 27, 2018 in connection with International Application No. PCT/JP2017/017823.

Torino et al., A microfluidic approach for inducing cell rotation by means of hydrodynamic forces. Sensors Aug. 19, 2016 vol. 16(8), E1326—12 pages.

Extended European Search Report dated May 28, 2019 in connection with European Application No. 17813053.0.

Hayakawa et al., On-chip 3D rotation of oocyte based on a vibration-induced local whirling flow. Microsystems & Nanoengineering. May 28, 2015 vol. 1(1); 9 pages.

Yalikun et al., A bio-manipulation method based on the hydrodynamic force of multiple microfluidic streams. Journal of Robotics and Mechatronics. Aug. 20, 2013 vol. 25(4); pp. 611-617.

Yalikun et al., A method of three-dimensional micro-rotational flow generation for biological applications. Micromachines. Aug. 10, 2016 vol. 7(8); 15 pages.

\* cited by examiner

APPARATUS, INFORMATION PROCESSING APPARATUS, PROGRAM, AND INFORMATION PROCESSING METHOD

CROSS-REFERENCE TO RELATED APPLICATIONS

This is a U.S. National Stage Application under 35 U.S.C. § 371, based on International Application No. PCT/JP2017/017823, filed in the Japanese Patent Office as a Receiving Office on May 11, 2017, entitled "DEVICE, INFORMATION PROCESSING DEVICE, PROGRAM, AND INFORMATION PROCESSING METHOD," which claims priority under 35 U.S.C. § 119(a)-(d) or 35 U.S.C. § 365(b) to Japanese Patent Application Number JP2016-116772, filed in the Japanese Patent Office on Jun. 13, 2016, each of which is hereby incorporated by reference in its entirety.

TECHNICAL FIELD

The present technology relates to an apparatus that is used to capture an image of a cell to obtain the image, an information processing apparatus, a program, and an information processing method.

BACKGROUND ART

There are known a technology of capturing an image of a cell to obtain the image (for example, see Patent Literature 1) and a technology of evaluating the quality of a cell on the basis of the obtained image of the cell (for example, see Patent Literature 2 and Patent Literature 3).

CITATION LIST

Patent Literature

Patent Literature 1: Japanese Patent Application Laid-open No. 2011-17620
Patent Literature 2: Japanese Patent Application Laid-open No. 2010-181402
Patent Literature 3: Japanese Patent Application Laid-open No. 2014-90692

DISCLOSURE OF INVENTION

Technical Problem

In a technology of evaluating the quality of a cell on the basis of an image of the cell obtained by capturing the image of the cell, it is desirable to increase the accuracy of evaluation more and more.

In view of the aforementioned circumstances, it is an object of the present technology to increase the accuracy of evaluation more and more, in a technology of evaluating the quality of a cell on the basis of an image of the cell obtained by capturing the image of the cell.

Solution to Problem

According to an embodiment of the present technology, there is provided an apparatus, including:
an accommodation unit capable of accommodating a cell and liquid; and
a rotation unit that produces a flow in the liquid in the accommodation unit to rotate the cell.

As a result, it is possible to rotate a cell automatically without manual operations of a user.

The rotation unit includes a first output port that produces a flow of the liquid in contact with a first portion in a first direction to rotate the cell around one axis, the first portion being a part of a surface of the cell.

In this manner, it is possible to rotate the cell by producing a flow of liquid in contact with at least a part of the surface of the cell.

The rotation unit further includes a second output port that produces a flow of the liquid in contact with a second portion in a second direction to prevent the cell rotating around the one axis from flowing in the first direction and to rotate the cell around the one axis, the second portion being another part of the surface of the cell, the second direction including a component of a direction opposite to the first direction.

Typically, the second output port produces a flow of the broth in contact with the second portion, which is symmetric to the first portion about the center point of the cell, in the second direction opposite to the first direction. As a result, the rotation axis of the cell is controlled such that the rotation axis passes through the center of the cell, and the cell may be rotated around the one axis more stably.

The apparatus further includes:
a rotation controller unit that
detects a rotation amount input from an input device, and
controls the flow of the liquid produced by each of the output ports on the basis of the input rotation amount to control a rotation amount of the cell.

As a result, a user is capable of rotating the cell by an arbitrary rotation amount by using the input device.

The rotation unit includes two or more pairs of the first output port and the second output port, and
the pairs are arranged such that the pairs are capable of rotating the cell around an axis including components of two orthogonal axes.

The rotation unit includes three or more pairs of the first output port and the second output port, and
the pairs are arranged such that the pairs are capable of rotating the cell around an axis including components of three orthogonal axes.

As a result, by rotating the cell, it is possible to observe a cell having a solid (three-dimensional) shape in a plurality of three-dimensional orientations.

The rotation controller unit
detects a rotation direction and a rotation amount input from the input device, and
controls the flow of the liquid produced by each of the output ports on the basis of the input rotation direction and the input rotation amount to control the rotation direction and the rotation amount of the cell.

As a result, a user is capable of rotating the cell in an arbitrary rotation direction by an arbitrary rotation amount by using the input device.

The apparatus further includes:
an image capturing unit that captures an image of the cell in the accommodation unit to obtain an image of the cell, in which
the rotation controller unit
calculates an actual rotation direction and an actual rotation amount of the cell on the basis of an image of the cell before rotation and an image of the cell after rotation captured by the image capturing unit, and
controls the flow of the liquid produced by each of the output ports on the basis of the actual rotation direction and the actual rotation amount calculated on the basis of the images of the cell to attain the input rotation direction and the input rotation amount.

In this manner, the actual rotation direction and the actual rotation amount calculated on the basis of images before and after rotation are used as feedback, and the rotation controller unit 130 keeps controlling the rotation unit until the input rotation direction and the input rotation amount are attained. As a result, it is possible to more reliably attain the rotation direction and rotation amount input from the input device (i.e., desired by user) in rotation of the cell.

Each of the output ports injects fluid into the liquid in the accommodation unit to produce the flow of the liquid in the accommodation unit.

Typically, liquid that is the same as the liquid in the accommodation unit may be injected from each output port to thereby produce a flow in the liquid in the accommodation unit. Alternatively, liquid different from the liquid in the accommodation unit or gas may be injected.

Each of the output ports vibrates the liquid in the accommodation unit to produce the flow of the liquid in the accommodation unit.

For example, ultrasound may be produced from each output port to vibrate the liquid in the accommodation unit.

According to an embodiment of the present technology, there is provided an information processing apparatus, including:

an image obtaining unit that obtains an image of a cell corresponding to a rotation direction and a rotation amount input from an input device; and an evaluation unit that evaluates the cell on the basis of the obtained image of the cell, in which the image obtaining unit obtains, as the image of the cell, an image based on an image of the cell obtained by an image capturing unit of an apparatus, the apparatus including an accommodation unit capable of accommodating the cell and liquid, a rotation unit that produces a flow in the liquid in the accommodation unit to rotate the cell, a rotation controller unit that controls the rotation unit to control the rotation direction and the rotation amount of the cell, and the image capturing unit that captures an image of the cell in the accommodation unit to obtain the image of the cell.

According to the present embodiment, since the quality of a cell is evaluated on the basis of image processing, it is possible to provide objective evaluation excluding subjective evaluation of a person to a user.

The rotation controller unit detects the rotation direction and the rotation amount input from the input device, and controls the rotation unit on the basis of the input rotation direction and the input rotation amount to control the rotation direction and the rotation amount of the cell, the image capturing unit obtains an image of the cell whose rotation direction and rotation amount are controlled on the basis of the input rotation direction and the input rotation amount, and the image obtaining unit obtains the image of the cell from the image capturing unit.

In this manner, the actual rotation direction and the actual rotation amount calculated on the basis of images before and after rotation are used as feedback, and the rotation controller unit 130 keeps controlling the rotation unit until the input rotation direction and the input rotation amount are attained. As a result, it is possible to more reliably attain the rotation direction and rotation amount input from the input device (i.e., desired by user) in rotation of the cell.

The image obtaining unit detects the rotation direction and the rotation amount input from the input device, and reads an image of the cell corresponding to the input rotation direction and the input rotation amount from a storage device that stores images of the cell obtained by the image capturing unit and rotation information about rotation directions and rotation amounts of the cell in association with each other, or reads a plurality of images from the storage device, combines the plurality of read images, and generates an image of the cell corresponding to the input rotation direction and the input rotation amount.

According to the present embodiment, since images of a cell rotated are stored, it is possible to three-dimensionally observe and evaluate the cell afterward. For example, if a cell is a zygote or an embryo, by storing images before the progress of cell division, it is possible to three-dimensionally compare and observe a past image and the present cell in the accommodation unit simultaneously.

According to an embodiment of the present technology, there is provided a program, that causes an information processing apparatus to operate as an image obtaining unit that obtains an image of a cell corresponding to a rotation direction and a rotation amount input from an input device; and an evaluation unit that evaluates the cell on the basis of the obtained image of the cell, in which the image obtaining unit obtains, as the image of the cell, an image based on an image of the cell obtained by an image capturing unit of an apparatus, the apparatus including an accommodation unit capable of accommodating the cell and liquid, a rotation unit that produces a flow in the liquid in the accommodation unit to rotate the cell, and the image capturing unit that captures an image of the cell in the accommodation unit to obtain the image of the cell.

According to an embodiment of the present technology, there is provided an information processing method, including:

by an image obtaining unit, obtaining an image of a cell corresponding to a rotation direction and a rotation amount input from an input device; and by an evaluation unit, evaluating the cell on the basis of the obtained image of the cell, in which the image obtaining unit obtains, as the image of the cell, an image based on an image of the cell obtained by an image capturing unit of an apparatus, the apparatus including an accommodation unit capable of accommodating the cell and liquid, a rotation unit that produces a flow in the liquid in the accommodation unit to rotate the cell, and the image capturing unit that captures an image of the cell in the accommodation unit to obtain the image of the cell.

Advantageous Effects of Invention

As described above, according to the present technology, in a technology of evaluating the quality of a cell on the basis of an image of the cell obtained by capturing the image of the cell, it is possible to increase the accuracy of evaluation more and more.

Note that the effects described here are not limitations, but any effects described in the present disclosure may be obtained.

MODE(S) FOR CARRYING OUT THE INVENTION

Hereinafter, embodiments of the present technology will be described with reference to the drawings.

(I. First Embodiment)

1. Configuration of Cell Evaluation Apparatus

Figure 1:
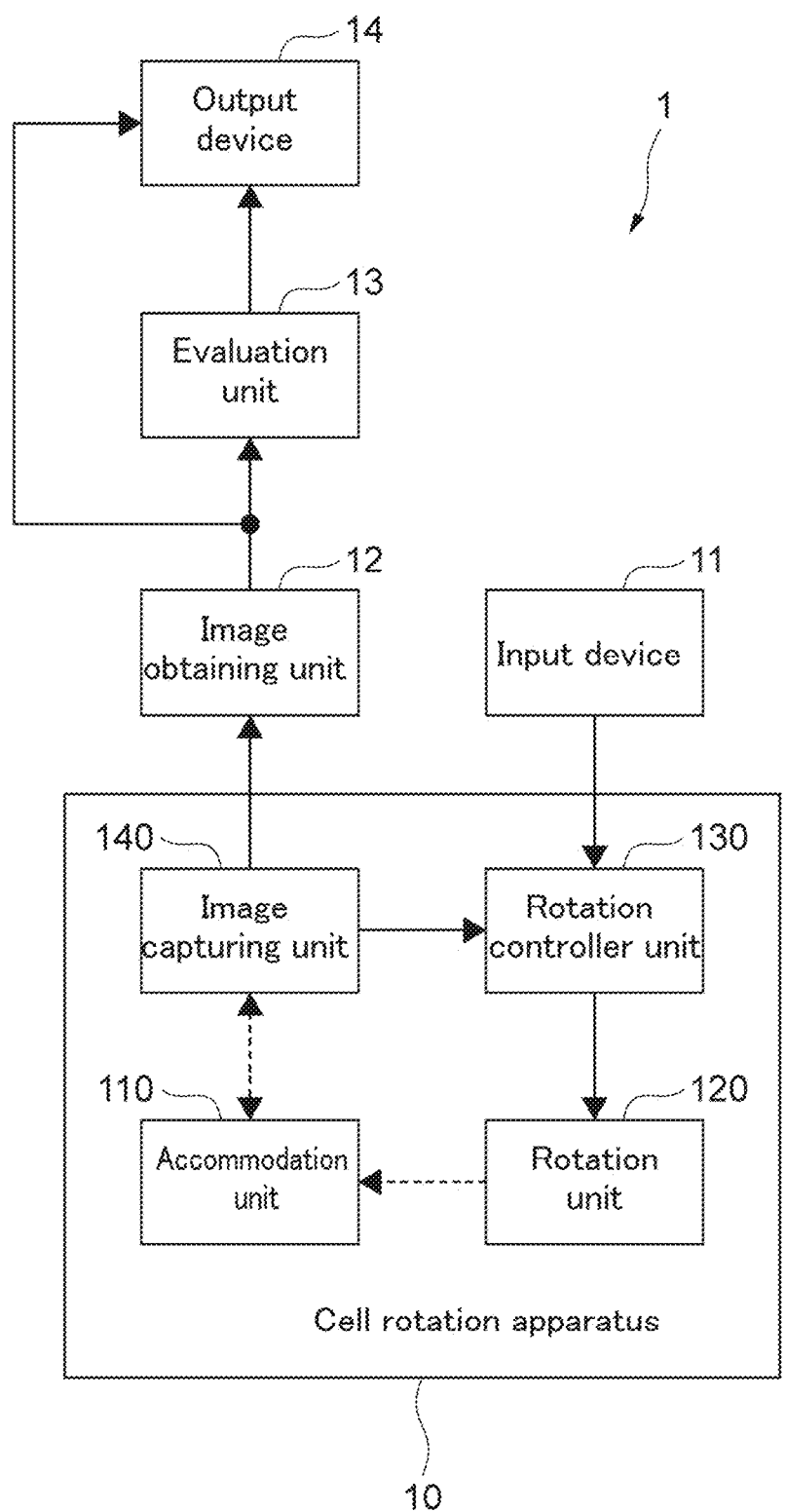
FIG. 1 A block diagram showing a configuration of a cell evaluation apparatus (information processing apparatus) of a first embodiment.

FIG. 1 is a block diagram showing a configuration of a cell evaluation apparatus (information processing apparatus) of a first embodiment.

In the present description, a "cell" (singular) conceptually includes at least a single cell and a mass of a plurality of cells. Examples of the "cell" at least include an unfertilized ovum (egg cell), a zygote, and an embryo of an organism, each of which has a solid (three-dimensional) shape.

The cell evaluation apparatus 1 includes the cell rotation apparatus 10 (apparatus), the input device 11, the image obtaining unit 12, the evaluation unit 13, and the output device 14.

A CPU (Central Processing Unit) loads a program recorded in a ROM (Read Only Memory), which is an example of a non-transitory computer readable recording medium, in a RAM (Random Access Memory) and executes the program to thereby realize at least the image obtaining unit 12 and the evaluation unit 13 of the cell evaluation apparatus 1 and the rotation controller unit 130 (described later) of the cell rotation apparatus 10.

The input device 11 is an apparatus capable of inputting a rotation direction and a rotation amount in three-axis directions. Examples of a device applicable to the input device 11 include a trackball, a touchpad, mouse, a keyboard, and the like. If a trackball is used as the input device 11, a user may input a rotation direction and a rotation amount in three-axis directions more intuitively than the other devices.

The cell rotation apparatus 10 includes the accommodation unit 110 capable of accommodating a cell and liquid, and the rotation unit 120 that rotates the cell in the accommodation unit on the basis of a rotation direction and a rotation amount in three-axis directions input from the input device 11. A more specific configuration of the cell rotation apparatus 10 will be described in detail later.

The image obtaining unit 12 obtains images in real time from an image capturing unit (described later), which continuously captures images of the cell in the accommodation unit of the cell rotation apparatus 10.

The evaluation unit 13 evaluates the cell on the basis of the images of the cell obtained by the image obtaining unit 12.

The output device 14 is at least a display device that outputs images such as a display, and may include a device that outputs sounds such as a speaker. The output device 14 as a display device displays the images of the cell obtained by the image obtaining unit 12 in real time. The output device 14 further outputs evaluation results of the cell by the evaluation unit 13 with images, sounds, and the like.

2. Configuration of Cell Rotation Apparatus

Figure 2:
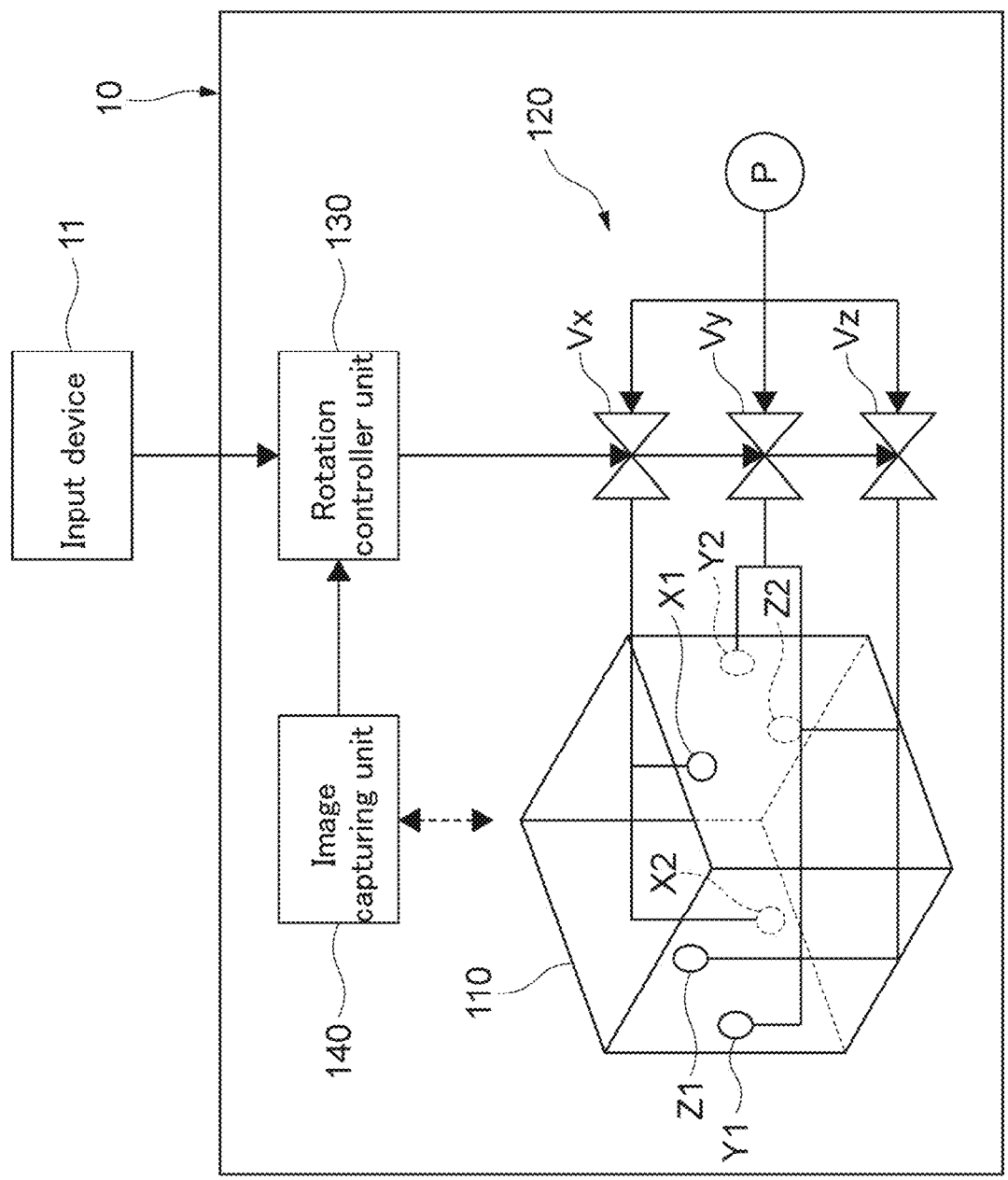
FIG. 2 A diagram schematically showing the cell rotation apparatus.

FIG. 2 is a diagram schematically showing the cell rotation apparatus.

The cell rotation apparatus 10 includes the accommodation unit 110, the rotation unit 120, the rotation controller unit 130, and the image capturing unit 140.

The accommodation unit 110 accommodates liquid, and is capable of accommodating one cell in the liquid and keeping the cell at a constant position. The "liquid" is, typically, broth appropriate for culturing a cell, and broth will be described as the liquid hereinafter. For example, the accommodation unit 110 may have a thin cylinder shape having an open top. Alternatively, a petri dish such as a schale may be divided into a matrix in a horizontal direction with a plurality of partitions, and the one schale may thereby have a plurality of accommodation units 110. In other words, one section of the matrix functions as one accommodation unit 110. One section of the matrix may have a square column or cylinder shape having an open top. Anyway, it is only necessary for the accommodation unit 110 to have a size and a shape such that the accommodation unit 110 is capable of accommodating one cell and keeping the cell at a constant position. Specifically, the accommodation unit 110 may have an approximately-hemispherical concave bottom, a diameter not too larger than a size of a cell, and a depth not too smaller than the size of the cell. In the following description, it does not matter how many accommodation unit(s) 110 is/are provided, and the one accommodation unit 110 will only be described.

The rotation unit 120 includes the pump P, the X-axis rotation valve Vx, the Y-axis rotation valve Vy, the Z-axis rotation valve Vz, the first X-axis jet port X1 (first output port), the second X-axis jet port X2 (second output port), the first Y-axis jet port Y1 (first output port), the second Y-axis jet port Y2 (second output port), the first Z-axis jet port Z1 (first output port), and the second Z-axis jet port Z2 (second output port). In the present description, "X-axis", "Y-axis", and "Z-axis" mean three orthogonal axes, and do not mean the horizontal directions and the vertical direction.

The first X-axis jet port X1, the second X-axis jet port X2, the first Y-axis jet port Y1, the second Y-axis jet port Y2, the first Z-axis jet port Z1, and the second Z-axis jet port Z2 are formed on inner-wall surfaces of the accommodation unit 110 (if there are a plurality of accommodation units 110, the jet ports are independently formed for each of all the accommodation units 110). Each of the first X-axis jet port X1, the second X-axis jet port X2, the first Y-axis jet port Y1, the second Y-axis jet port Y2, the first Z-axis jet port Z1, and the second Z-axis jet port Z2 jets out (injects) fluid in broth in the accommodation unit 110 to thereby produce a flow in the broth in the accommodation unit 110. The "fluid" is, typically, liquid that is the same as the broth in the accommodation unit 110, but may be liquid different from the broth of the accommodation unit 110 or gas.

The pump P is connected to the first X-axis jet port X1, the second X-axis jet port X2, the first Y-axis jet port Y1, the second Y-axis jet port Y2, the first Z-axis jet port Z1, and the second Z-axis jet port Z2 via flow paths, and supplies the broth to the jet ports. A part (part at not pump side but jet port side) of each flow path is formed inside a wall surface of the accommodation unit 110 (if there are a plurality of accommodation units 110, the flow paths are independently formed for each of all the accommodation units 110).

The X-axis rotation valve Vx is provided on the flow path connecting the pump P, and the first X-axis jet port X1 and the second X-axis jet port X2. The Y-axis rotation valve Vy is provided on the flow path connecting the pump P, and the first Y-axis jet port Y1 and the second Y-axis jet port Y2. The Z-axis rotation valve Vz is provided on the flow path connecting the pump P, and the first Z-axis jet port Z1 and the second Z-axis jet port Z2.

The rotation controller unit 130 detects a rotation direction and a rotation amount input from the input device 11, and controls flows of the broth produced by the jet ports X1, X2, Y1, Y2, Z1, and Z2 independently on the basis of the input rotation direction and the input rotation amount to thereby control the rotation direction and the rotation amount of the cell C. Specifically, the rotation controller unit 130 controls the X-axis rotation valve Vx to open and close the X-axis rotation valve Vx to thereby control a jet speed and a jet volume of the broth jetted from the first X-axis jet port X1 and the second X-axis jet port X2. The rotation controller unit 130 controls the Y-axis rotation valve Vy to open and close the Y-axis rotation valve Vy to thereby control a jet speed and a jet volume of the broth jetted from the first Y-axis jet port Y1 and the second Y-axis jet port Y2. The rotation controller unit 130 controls the Z-axis rotation valve Vz to open and close the Z-axis rotation valve Vz to thereby control a jet speed and a jet volume of the broth jetted from the first Z-axis jet port Z1 and the second Z-axis jet port Z2. A method of calculating "a jet speed and a jet volume of the broth" will be described in more detail later.

The image capturing unit 140 at least includes an optical microscope and an image sensor, and captures optical microscopic images by using the image sensor. The image capturing unit 140 continuously captures images of the cell C in the accommodation unit 110 to obtain the images of the cell C. The image capturing unit 140 supplies the continuously-obtained images of the cell C to the rotation controller unit 130 in real time.

The rotation controller unit 130 calculates a rotation direction and a rotation amount of the cell C on the basis of the images of the cell C obtained by the image capturing unit 140, which continuously captures the images of the cell C.

The rotation controller unit 130 controls flows of the broth produced by the jet ports X1, X2, Y1, Y2, Z1, and Z2 independently on the basis of the rotation direction and the rotation amount calculated on the basis of the cell C to attain the rotation direction and the rotation amount input from the input device 11.

3. Relation Between Cell and Flows of Broth

Figure 3:
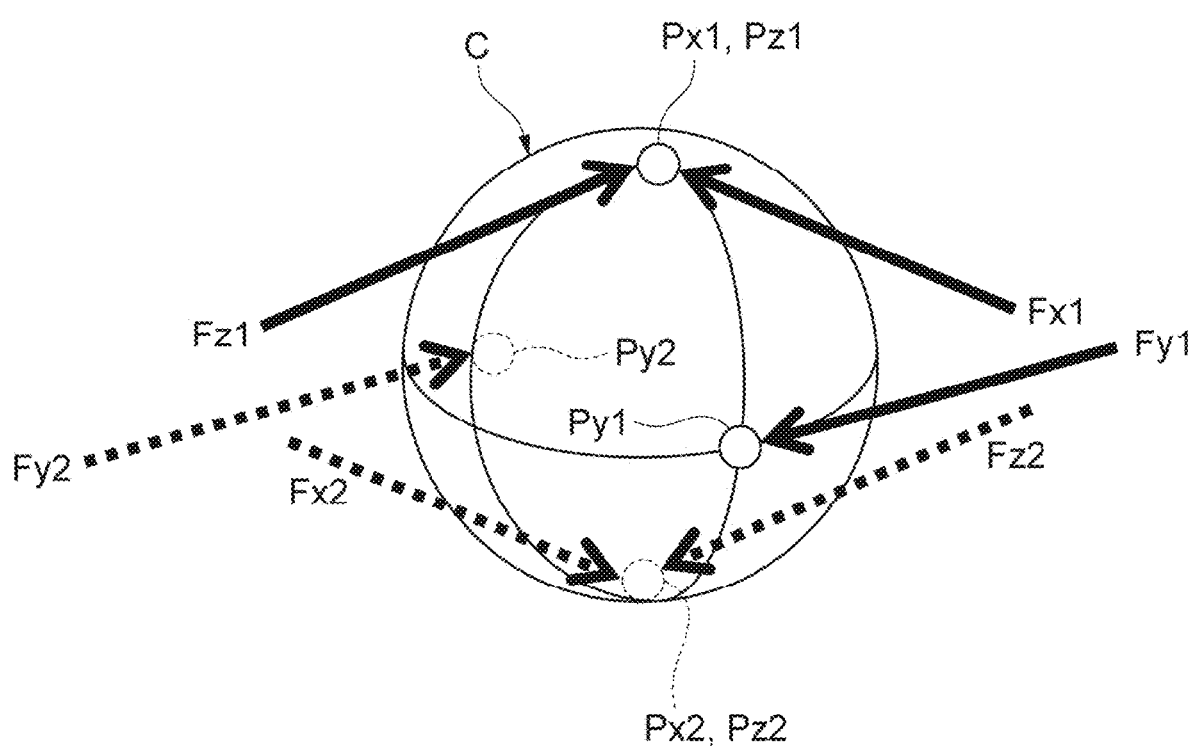
FIG. 3 A diagram schematically showing relations between a cell in the accommodation unit and flows of broth.

FIG. 3 is a diagram schematically showing relations between a cell in the accommodation unit and flows of broth.

Flows of broth in the accommodation unit 110 produced by the jet ports X1, X2, Y1, Y2, Z1, and Z2 and a rotation direction of the cell C will be described more specifically. FIG. 3 shows, for convenience, curves on the approximately-spherical cell C showing rotation directions around the three axes.

The first X-axis jet port X1 produces the flow Fx1 of the broth in contact with the first portion Px1, which is a part of the surface of the cell C in the accommodation unit 110, in one direction (first direction) in the X axis to thereby rotate the cell C around one axis passing through the first portion Px1. The second X-axis jet port X2 produces the flow Fx1 of the broth in contact with the second portion Px2, which is another part of the surface of the cell C, in a direction (second direction) including a component of a direction opposite to the one direction in the X axis to prevent the cell C rotating around the one axis passing through the first portion Px1 from flowing in the one direction in the X axis and to rotate the cell C around the one axis passing through the first portion Px1. Typically, the second X-axis jet port X2 produces a flow of the broth in contact with the second portion Px2, which is symmetric to the first portion Px1 about the center point of the cell C, in the direction (second direction) opposite to the one direction in the X axis. As a result, the rotation axis of the cell C (one axis passing through the first portion Px1) is controlled such that the rotation axis passes through the center of gravity of the cell C, the position of the cell C is stable, and the cell C may be rotated around the one axis passing through the first portion Px1 and the second portion Px2 stably.

The first Y-axis jet port Y1 produces the flow Fy1 of the broth in contact with the first portion Py1, which is a part of the surface of the cell C in the accommodation unit 110, in one direction (first direction) in the Y axis to thereby rotate the cell C around one axis passing through the first portion Py1. The second Y-axis jet port Y2 produces the flow Fy1 of the broth in contact with the second portion Py2, which is another part of the surface of the cell C, in a direction (second direction) including a component of a direction opposite to the one direction in the Y axis to prevent the cell C rotating around the one axis passing through the first portion Py1 from flowing in the one direction in the Y axis and to rotate the cell C around the one axis passing through the first portion Py1. Typically, the second Y-axis jet port Y2 produces a flow of the broth in contact with the second portion Py2, which is symmetric to the first portion Py1 about the center point of the cell C, in the direction (second direction) opposite to the one direction in the Y axis. As a result, the rotation axis of the cell C (one axis passing through the first portion Py1) is controlled such that the rotation axis passes through the center of the cell C, the position of the cell C is stable, and the cell C may be rotated around the one axis passing through the first portion Py1 and the second portion Py2 stably.

The first Z-axis jet port Z1 produces the flow Fz1 of the broth in contact with the first portion Pz1, which is a part of the surface of the cell C in the accommodation unit 110, in one direction (first direction) in the Z axis to thereby rotate the cell C around one axis passing through the first portion Pz1. The second Z-axis jet port Z2 produces the flow Fz1 of the broth in contact with the second portion Pz2, which is another part of the surface of the cell C, in a direction (second direction) including a component of a direction opposite to the one direction in the Z axis to prevent the cell C rotating around the one axis passing through the first portion Pz1 from flowing in the one direction in the Z axis and to rotate the cell C around the one axis passing through the first portion Pz1. Typically, the second Z-axis jet port Z2 produces a flow of the broth in contact with the second portion Pz2, which is symmetric to the first portion Pz1 about the center point of the cell C, in the direction (second direction) opposite to the one direction in the Z axis. As a result, the rotation axis of the cell C (one axis passing through the first portion Pz1) is controlled such that the rotation axis passes through the center of the cell C, the position of the cell C is stable, and the cell C may be rotated around the one axis passing through the first portion Pz1 and the second portion Pz2 stably.

Note that, in order to rotate the cell C in both the clockwise and anticlockwise directions in each of the three axes accurately and easily, there may be provided two sets (not shown) of the rotation units 120 (each including the pump P, the X-axis rotation valve Vx, the Y-axis rotation valve Vy, the Z-axis rotation valve Vz, the first X-axis jet port X1, the second X-axis jet port X2, the first Y-axis jet port Y1, the second Y-axis jet port Y2, the first Z-axis jet port Z1, and the second Z-axis jet port Z2). In other words, the one accommodation unit 110 may include a first rotation unit for rotating the cell C in the clockwise direction and a second rotation unit for rotating the cell C in the anticlockwise direction, and the rotation controller unit 130 may control the first and second rotation units independently.

4. Method of Calculating Jet Speed and Jet Volume of Broth

A specific example of a method of calculating a jet speed and a jet volume of the broth by the rotation controller unit 130 will be described.

From the viewpoint of the physics analysis, control of a jet speed and a jet volume of broth may be determined on the basis of a moment of inertia, which is calculated on the basis of a size and a mass of a cell. The moment of inertia of a cell is calculated by Math 1, where the cell is approximated to a sphere, a is a radius of the cell, and M is a mass.

$$I = \tfrac{2}{5} M a^2 \qquad [\text{Math 1}]$$

According to a conceivable method, a volume of jetted broth and a jet speed are determined with reference to the moment of inertia. However, in fact, it is difficult to control the jetted liquid appropriately on the basis of an analytical calculation method because of friction between jetted liquid and broth, friction between a cell and the broth, and an uneven mass of the cell. In view of the aforementioned circumstances, a method of machine-learning those elements will be described. An analytical jet volume and speed of Math 1 may be used as an initial value of a jet volume in creating learning data of the machine learning.

d [m/s] is a jet speed of a jet port, e [m^2] is a cross-sectional area of the jet port, g [sec] is a jet time period, and r [rad] is a rotation angle in the jet time period. The cross-sectional area e of a jet port is a fixed value depending on a schale, and the jet speed d is also a fixed value for simplifying the apparatus. Then, various different combinations of the variables g and r are obtained through experiments. Regression learning is executed to estimate the jet time period g where the desired rotation angle r is given. As a result, the jet time period for controlling rotation of a cell may be determined. For example, the following linear regression may be used for regression learning. Where a polynomial basis is used as a basis function, the basis function may be represented as follows.

$$\phi_i(x) = x^i \qquad [\text{Math 2}]$$

A function represented by a linear combination by using the basis functions is as follows. M is the number of basis functions that are used.

$$f(x) = \sum_{i=0}^{M-1} w_i \phi_i(x) \qquad [\text{Math 3}]$$

In this example, in Math 3, x is the desired rotation angle r, and the function f(x) obtained by linear regression is the jet time period obtained by linear regression. w of Math 3 is calculated as follows. w of the following mathematical expression, where E(w) is the smallest value, is calculated by using a plurality (here, the number is N) of sets $(g_n, r_n)$ of data of the jet time period g obtained through experiments and the rotation angle r obtained on the basis of the jet time period g.

$$E(w) = \frac{1}{2}\sum_{n=1}^{N}(f(r_n) - g_n)^2 + \frac{1}{2}\lambda\sum_{i=1}^{M} w_i^2 = \qquad [\text{Math 4}]$$
$$\frac{1}{2}\sum_{n=1}^{N}\left(\sum_{i=0}^{M-1} w_i r_n^i - g_n\right)^2 + \frac{1}{2}\lambda\sum_{i=1}^{M} w_i^2$$

In order to actually calculate the function f(x) by using linear regression and by using Math 4, an appropriate weight (e.g., 0.1) is substituted in λ of Math 4, and the N sets $(g_n, r_n)$ of data of the jet time period g and the rotation angle r obtained through experiments are substituted in Math 4. An equation system, where a partial derivative value of $w_i$ is 0, is calculated. The calculated $w_i$ is substituted in Math 3, and a desired function f(x) may be calculated.

As the regression calculation, not only the linear regression but also general regression learning methods such as support vector regression and logistic regression may be used and realized.

Further, in order to learn the estimation of a jet time period, information such as a shape and a size of a cell may be obtained from image information of the cell, and learning may be executed by using those parameters. Also, an appropriate position and an appropriate angle of a broth jet may be determined on the basis of recognition process based on image recognition and machine learning. For example, the rotation controller unit 130 may determine a shape and a size of a cell on the basis of image recognition, and may change an angle and a position of a broth jet on the basis of the determination result.

5. Operation of Cell Evaluation Apparatus

Figure 4:
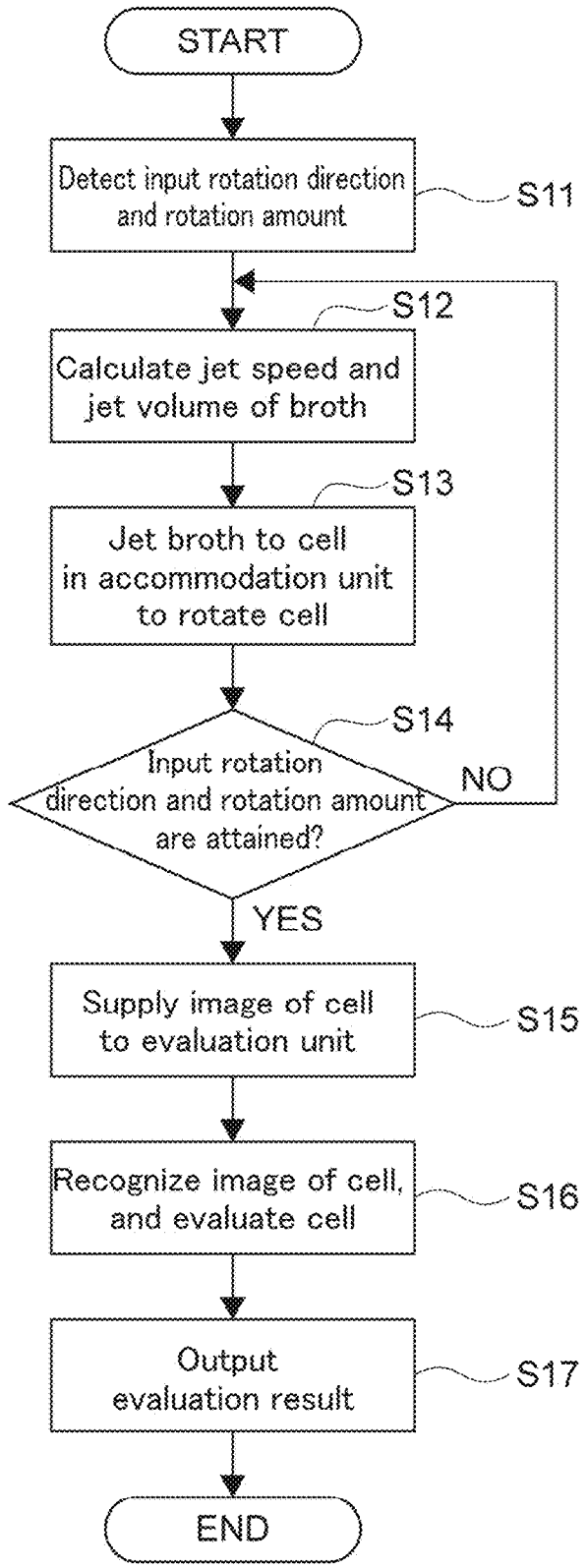
FIG. 4 A flowchart showing an operation of the cell evaluation apparatus.

FIG. 4 is a flowchart showing an operation of the cell evaluation apparatus.

Before the operation, the accommodation unit 110 accommodates the cell C and broth. The image capturing unit 140 captures images of the cell C in the accommodation unit 110 continuously (at regular intervals) to obtain images of the cell C. The image capturing unit 140 at least supplies an image of the cell C before rotation to the rotation controller unit 130, and further supplies continuously-obtained images of the cell C to the image obtaining unit 12 continuously in real time. The image obtaining unit 12 outputs the images of the cell C obtained from the image capturing unit 140 to the output device 14 (display device) continuously in real time. As a result, the output device (display device) displays the images of the cell C in the accommodation unit 110 in time series continuously in real time. A user, who is observing images of the cell C displayed on the output device 14 (display device) in real time, wishes to watch the cell C in a different direction. Then, the user operates the input device 11, and inputs a rotation direction (direction including components of three axes) and a rotation amount for rotation of the cell C.

The rotation controller unit 130 detects the rotation direction (direction including components of three axes) and the rotation amount input from the input device (Step S11). The rotation controller unit 130 calculates a jet speed and a jet volume of the broth in each of the three-axis directions by using the aforementioned calculation method such that the rotation direction and the rotation amount input from the input device 11 is attained (Step S12). The rotation controller unit 130 controls the X-axis rotation valve Vx, the Y-axis rotation valve Vy, and the Z-axis rotation valve Vz of the rotation unit 120 to independently open and close the X-axis rotation valve Vx, the Y-axis rotation valve Vy, and the Z-axis rotation valve Vz of the rotation unit 120 in order to attain the calculated jet speed and the calculated jet volume of the broth in each of the three-axis directions. As a result, the first X-axis jet port X1 and the second X-axis jet port X2, the first Y-axis jet port Y1 and the second Y-axis jet port Y2, and the first Z-axis jet port Z1 and the second Z-axis jet port Z2 jet the broth to the cell C in the accommodation unit 110 with independent jet speeds and jet volumes. As a result, the cell C in the accommodation unit 110 rotates on the basis of the rotation direction and the rotation amount input from the input device 11 (Step S13). The image capturing unit 140 at least supplies an image of the cell C after rotation to the rotation controller unit 130 out of the images of the cell C captured and obtained continuously (at regular intervals).

The rotation controller unit 130 compares the image of the cell C before rotation with the image of the cell C after rotation, which are obtained from the image capturing unit 140, and calculates an actual rotation direction and an actual rotation amount of the cell C. Specifically, the rotation controller unit 130 extracts an interest point in the image of the cell C before rotation and an interest point in the image of the cell C after rotation (the respective interest points are the same positions of the cell C). The rotation controller unit 130 compares the interest point in the image of the cell C before rotation with the interest point in the image of the cell C after rotation, and calculates a rotation direction and a rotation amount of the interest point. The rotation controller unit 130 determines the calculated rotation direction and the calculated rotation amount of the interest point as the actual rotation direction and the actual rotation amount of the cell C. The rotation controller unit 130 compares the rotation direction and rotation amount calculated on the basis of the images of the cell C before and after rotation with the rotation direction and the rotation amount input from the input device 11 (Step S14).

If the rotation direction and rotation amount calculated on the basis of the images of the cell C before and after rotation are not the same as the rotation direction and the rotation amount input from the input device 11, the rotation controller unit 130 determines that the input rotation direction and rotation amount are not attained (Step S14, NO). So the rotation controller unit 130 again calculates a jet speed and a jet volume of the broth in each of the three-axis directions in order to attain the rotation direction and the rotation amount input from the input device 11 (Step S12). Specifically, the rotation controller unit 130 calculates a displaced position, in an image, of the interest point in the image of the cell C before rotation, where it is assumed that the cell C before rotation is rotated with the rotation direction and the rotation amount input from the input device 11. The predicted position of the interest point will be referred to as "interest point predicted position". The rotation controller unit 130 compares the position of the interest point in the image of the cell C after rotation with the interest point predicted position, and calculates a rotation direction and a rotation amount required for the interest point in the image of the cell C after rotation to be displaced to the interest point predicted position. The rotation controller unit 130 calculates a jet speed and a jet volume of the broth in each of the three-axis directions by using the aforementioned calculation method such that the calculated rotation direction and the calculated rotation amount are attained. Steps S12 to S14 are repeated until the rotation controller unit 130 determines that the input rotation direction and the input rotation amount are attained (Step S14, YES).

If the rotation controller unit 130 determines that the input rotation direction and the input rotation amount are attained (Step S14, YES), the rotation controller unit 130 informs the image obtaining unit 12 of that. If the image obtaining unit 12 receives the information, the image obtaining unit 12 supplies the images of the cell C obtained from the image capturing unit 140 continuously in real time to the evaluation unit 13 in real time (Step S15). The evaluation unit 13 recognizes the obtained images of the cell C by image processing, and evaluates the quality of the cell C with reference to a known database (Step S16). A specific example of the evaluation method will be described later. The evaluation unit 13 causes the output device 14 to output the evaluation result by using a predetermined output method (display image or output sound) (Step S17). A specific example of the output method will be described later. As a result, a user recognizes the evaluation result of the quality of the cell C output from the output device 14.

6. Cell Evaluation Method

A specific example of a method of recognizing the image of the cell C after rotation by image processing and evaluating the quality of the cell C by the evaluation unit 13 (Step S16) will be described. For example, the cell C is a zygote (embryo). The cell C may be evaluated by using indicators generally used to evaluate the initial stages of embryogenesis, and have a grade (grade 1 is highest, and grade 5 is lowest) out of the following five stages. For example, the evaluation unit 13 recognizes forms of blastomeres and fragmentation in an image by using an edge detection technology, and evaluates the cell C on the basis of the recognized image to give a grade out of the five stages to the cell C.

Grade 1: Equal size blastomeres. No fragmentation.
Grade 2: Some unequal size blastomeres. Small fragmentation.

Grade 3: Unequal size blastomeres.

Grade 4: Equal size or unequal size blastomeres. Large fragmentation.

Grade 5: Defects of blastomeres. Largest fragmentation.

Alternatively, for example, if the cell C is a zygote (embryo) of a wagyu cattle, the cell C may be evaluated by using indicators generally used to evaluate the meat quality of wagyu cattle. In other words, the future meat quality of the cell C (zygote (embryo) of wagyu cattle) may be predicted. The cell C may be evaluated by using the indicators of the yield rank (three stages: highest A to lowest C) and the meat quality rank (five stages: highest 5 to lowest 1).

7. Method of Outputting Evaluation Result of Cell

Each of specific examples of a method of outputting an evaluation result of the quality of the cell C (Step S17) will be described.

Figure 5:
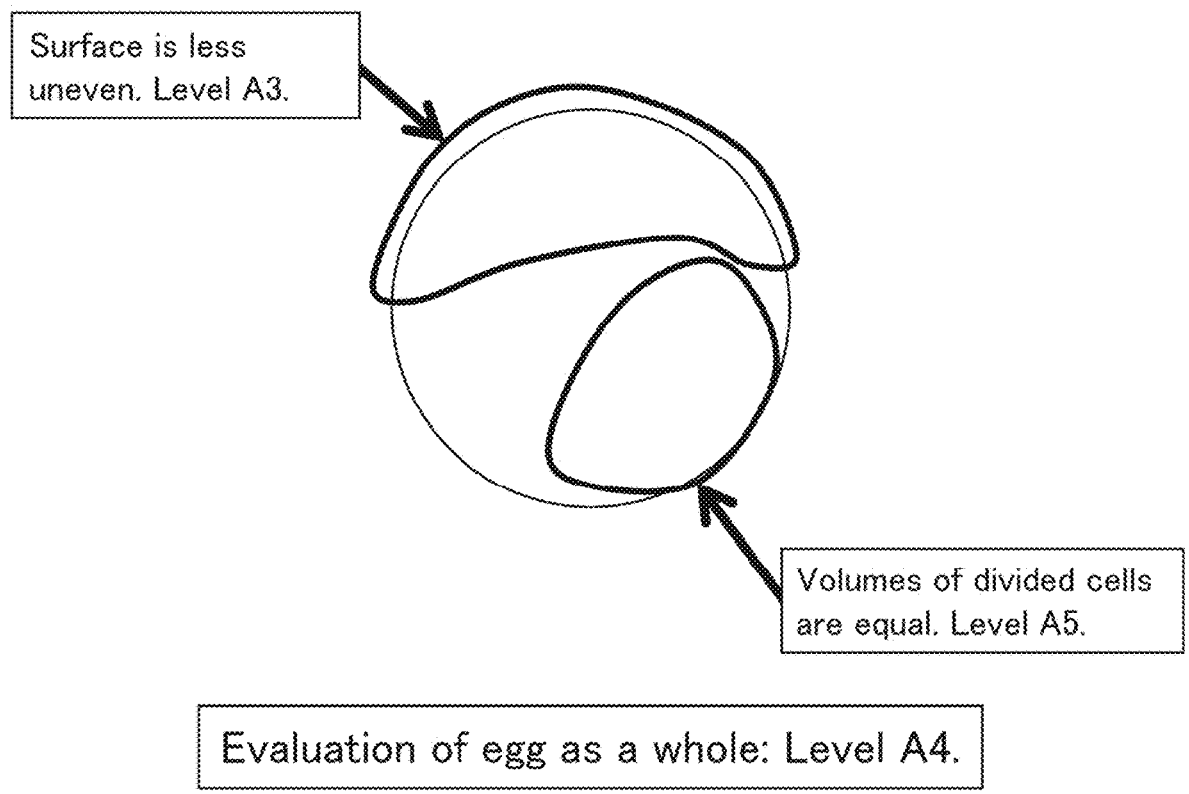
FIG. 5 A diagram illustrating a specific example of a method of outputting an evaluation result of the quality of the cell.

FIG. 5 is a diagram illustrating a specific example of a method of outputting an evaluation result of the quality of the cell.

The evaluation unit 13 extracts, by image processing, a portion, in which surface is less uneven, and a portion, in which volumes of divided cells are equal, from an image of the cell C. In a known database, the evaluation result A3 is registered for the portion, in which surface is less uneven, the evaluation result A5 is registered for the portion, in which volumes of divided cells are equal, and the like. The evaluation unit 13 reads, from the database, the evaluation result in association with the feature of each portion extracted by image processing. The evaluation unit 13 combines the image of the cell C and the information about the evaluation result and the like on the basis of the position information of each portion extracted by image processing and the read evaluation result to thereby generate a combination image. The evaluation unit 13 causes the output device 14 (display device) to display the generated combination image. FIG. 5 shows an example of the combination image. In FIG. 5, the image of the cell C, the evaluation results (A3, A5) and the evaluation reasons (in this example, text) of the respective portions, and the evaluation result (A4) of the cell C as a whole are combined.

Figure 6:
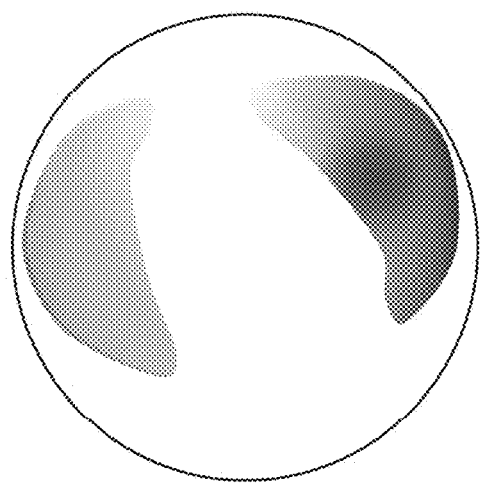
FIG. 6 A diagram illustrating another specific example of a method of outputting an evaluation result of the quality of the cell.

FIG. 6 is a diagram illustrating another specific example of a method of outputting an evaluation result of the quality of the cell.

The evaluation unit 13 evaluates images of the cell C obtained from the image obtaining unit 12 continuously in real time, and is thereby capable of evaluating the cell C in time series. Specifically, the evaluation unit 13 recognizes the series of images of the cell C obtained from the image obtaining unit 12 by edge detection and the like, and recognizes a portion, whose images are changed greatly, as a portion having a great dynamic change during cell division. The evaluation unit 13 combines the series of images of the cell C obtained from the image obtaining unit 12 and color gradation (which may be full color, or black and white) showing position information of that portion and the like to generate combination images. The evaluation unit 13 causes the output device 14 (display device) to display the generated combination images. FIG. 6 shows an example of a combination image. In FIG. 6, in the image of the cell C, portions having great dynamic changes are colored with darkness depending on change degrees.

When evaluating the quality of a zygote (embryo), one of important references is an appearance of division in time series during cell division such as the balance of the sizes of blastomeres after cleavage and the amount of fragmentation.

By virtually applying color gradation depending on dynamic changes of cleavage, a user visually determines the quality of a zygote (embryo) easily. Further, dynamic information such as cleavage of a zygote (embryo) may be used to determine the quality of the cell. Note that, as dynamic change information, not only two-dimensional information from two-dimensional images, but also three-dimensional information of dynamic changes obtained by using a sensor capable of obtaining three-dimensional information such as a stereo camera may be used. As a result, evaluation may be made on the basis of detailed information. Further, color gradation may be made and displayed on the basis of not only dynamic changes but also information of an inner cell mass such as density information.

Alternatively, dynamic changes of a zygote (embryo) may be emphasized and expressed by not only color gradation but also sounds. The evaluation unit 13 may recognize a series of images of the cell C obtained from the image obtaining unit 12 by edge detection and the like, detect an image having a great dynamic change, and then cause the output device 14 being a speaker to output some sounds. For example, the pitch, the volume, and the tone of sounds are in association with the speed of dynamic changes of the texture during cell division. As a result, a user may evaluate a zygote (embryo) on the basis of not only visual information of images but also audio information.

Figure 7:
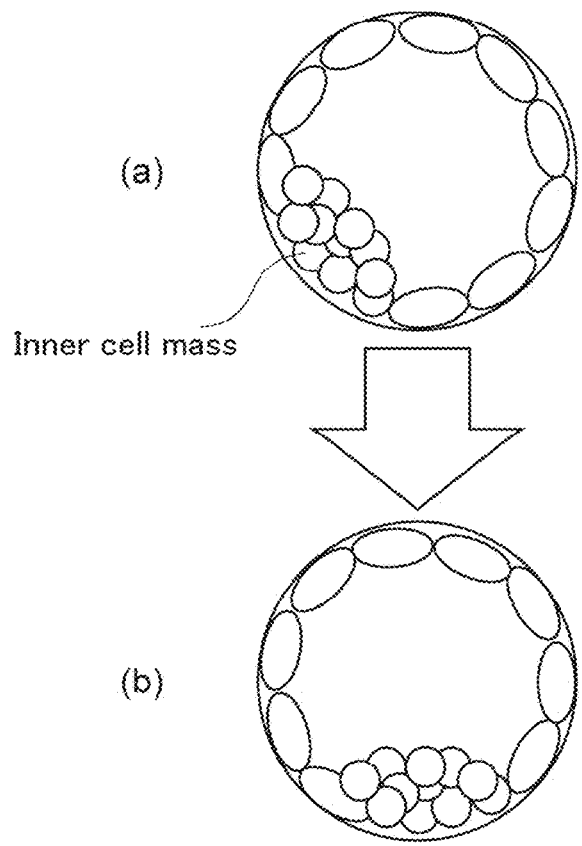
FIG. 7 A diagram illustrating another specific example of a method of outputting an evaluation result of the quality of the cell.

FIG. 7 is a diagram illustrating another specific example of a method of outputting an evaluation result of the quality of the cell.

The evaluation unit 13 detects a feature portion (for example, boundary between cells after cell division, or inner cell mass) useful for evaluation from an image (FIG. 7, image a) of the cell C by image recognition such as edge detection. The evaluation unit 13 the evaluation unit 13 rotates the image of the cell C in an orientation with which a user may visually recognize the image easily (FIG. 7, image b). Orientations of the cell C of a series of images of the cell C displayed in time series may change spontaneously as a result of cell division. However, if the cell C in the images is rotated to have the constant orientation by image recognition, a user visually recognizes the cell C easily.

Figure 8:
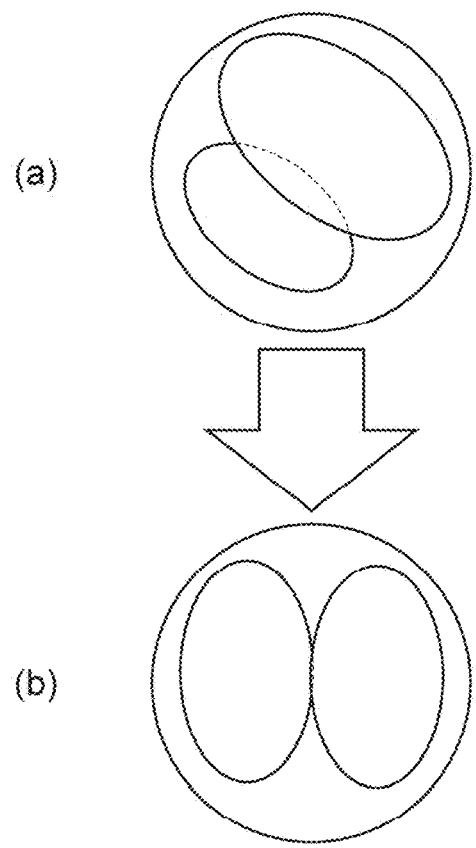
FIG. 8 A diagram illustrating another specific example of a method of outputting an evaluation result of the quality of the cell.

FIG. 8 is a diagram illustrating another specific example of a method of outputting an evaluation result of the quality of the cell.

In the example of FIG. 7, an image of the cell C is rotated two-dimensionally to have an orientation with which a user visually recognizes the image easily. Meanwhile, the cell C itself in the accommodation unit 110 may be rotated three-dimensionally, and an image of the rotated cell C may be displayed. As a result, the image of the cell C having an orientation, with which a user visually recognizes the image easily, may be displayed.

For example, the evaluation unit 13 determines that the two cells of the two-cell stage embryo (the cell C) of an image (FIG. 8, image a) overlap each other by image recognition such as edge detection. A user may observe the two cells more easily if the two cells do not overlap each other but are side-by-side. The evaluation unit 13 calculates, on the basis of the image, a rotation direction and a rotation amount of the cell C (two cells overlap each other) of the image such that the two cells will be side-by-side. The evaluation unit 13 informs the rotation controller unit 130 of the calculated rotation direction and the calculated rotation amount. The rotation controller unit 130 calculates a jet speed and a jet volume of the broth in each of the three-axis directions such that the obtained rotation direction and rotation amount are attained (similar to Step S12). The rotation unit 120 rotates the cell C (similar to Step S13). If the cell C has the desired posture (similar to Step S14, YES), the evaluation unit 13 outputs an image (FIG. 8, image b) of the cell C to the output device 14 (Step S17).

8. Conclusion

In order to observe a cell while rotating the cell, for example, according to a conceivable method, a two-dimensional image is rotated two-dimensionally. However, according to this method, a user cannot observe the cell in a plurality of three-dimensional orientations. Therefore, it is difficult to observe and evaluate the cell with a high degree of accuracy. Meanwhile, in order to observe a cell having a solid (three-dimensional) shape in a plurality of three-dimensional orientations, for example, the following methods are conceivable. For example, according to a conceivable method, a user produces a flow in broth manually by using a pipette or the like, and observes a cell in the broth by using a microscope while rotating the cell. However, it is difficult to rotate a cell in an appropriate orientation accurately. According to another example of a conceivable method, two image pickup apparatuses obtain images (stereo images) of a cell while the optical distance of the cell is being changed without rotating the cell, and the images are combined to generate a three-dimensional image. However, since a cell is not perfectly transparent, it is difficult to generate sharp images in directions different from the image-pickup direction.

To the contrary, according to the present embodiment, the rotation controller unit 130 controls the rotation unit 120 (Step S13) such that the rotation direction and rotation amount input from the input device (Step S11) are attained (Step S12). Then, the rotation controller unit 130 compares the actual rotation direction and the actual rotation amount calculated on the basis of images of the cell C before and after rotation with the rotation direction and rotation amount input from the input device 11 (Step S14). The rotation controller unit 130 keeps controlling the rotation unit 120 until the input rotation direction and the input rotation amount are attained (Step S14, YES).

As a result, it is possible to observe a cell having a solid (three-dimensional) shape in a plurality of three-dimensional orientations while rotating the cell. Further, the actual rotation direction and the actual rotation amount calculated on the basis of images before and after rotation are used as feedback, and the rotation controller unit 130 keeps controlling the rotation unit 120 until the input rotation direction and the input rotation amount are attained. As a result, it is possible to more reliably attain the rotation direction and rotation amount input from the input device 11 (i.e., desired by user) in rotation of the cell. Further, if a trackball is used as the input device 11, a user may input a rotation direction and a rotation amount in three-axis directions more intuitively than the other devices. In addition, the user may observe a cell intuitively as if the user grabs and rotates the cell.

Further, as a method of evaluating the quality of a cell by image recognition, for example, according to a conceivable method, a circumferential length value of the cell, an area value of the cell, and the like are obtained by image processing. However, those raw values are not evaluation values of the quality of a cell, but a person has to determine and evaluate the quality on the basis of those values. If a person determines and evaluates the quality, it is inevitable that evaluation has nonuniformity. According to another conceivable method, for example, an evaluation value of the quality of a cell as a whole is obtained. However, even if an evaluation value of the quality of a cell as a whole is obtained, it may be not easy for a user to understand the grounds and reasons of the evaluation value.

To the contrary, according to the present embodiment, the evaluation unit 13 extracts portions of the cell, each of which has a feature surface shape or volume, from an image of the cell C by image processing. The evaluation unit 13 reads an evaluation result in association with the feature of each portion extracted by image processing from a database. The evaluation unit 13 combines the image of the cell and information indicating the evaluation result and the like on the basis of the position information of each portion extracted by image processing and the read evaluation result to thereby generate a combination image (FIG. 5, FIG. 6).

As described above, further, since an image of a cell is rotated in an orientation, with which a user evaluates the cell easily (FIG. 7, FIG. 8), a user may visually observe the cell easily.

9. Modification Examples

According to the present embodiment, fluid (broth) is injected into the broth in the accommodation unit 110 from each of the jet ports X1, X2, Y1, Y2, Z1, and Z2 (output ports) to thereby produce flows in the broth in the accommodation unit 110. Alternatively, for example, ultrasound may be produced from each jet port to vibrate the broth in the accommodation unit 110 to thereby produce flows in the broth in the accommodation unit 110.

According to the present embodiment, the evaluation unit 13 recognizes an image of a cell by image processing, evaluates the quality of the cell with reference to a known database (Step S16), and causes the output device 14 to output the evaluation result (Step S17). The respective steps of evaluation may be omitted, and the evaluation unit 13 may only cause the output device 14 to output an image of the cell, in which the input rotation direction and the input rotation amount are attained.

II. Second Embodiment

1. Outline of Second Embodiment

In the first embodiment, a cell is rotated in real time on the basis of a rotation direction and a rotation amount input from the input device 11, images of the rotating cell are output to the output device 14 in real time, and the cell is evaluated in real time. To the contrary, according to a second embodiment, images of a cell rotated on the basis of a rotation direction and a rotation amount input from an input device are stored to thereby structure a database for realizing three-dimensional images. After that, an image of a cell corresponding to a rotation direction and a rotation amount input from the input device is read from the database, and the cell is evaluated. As a result, it is possible to observe an image of a cell three-dimensionally, which are captured in the past and stored.

In the following description, hardware configuration, respective functional units, and operational steps similar to those described in the first embodiment will be denoted by similar reference symbols, description thereof will be omitted, and different points will mainly be described.

2. Configuration of Cell Evaluation Apparatus

Figure 9:
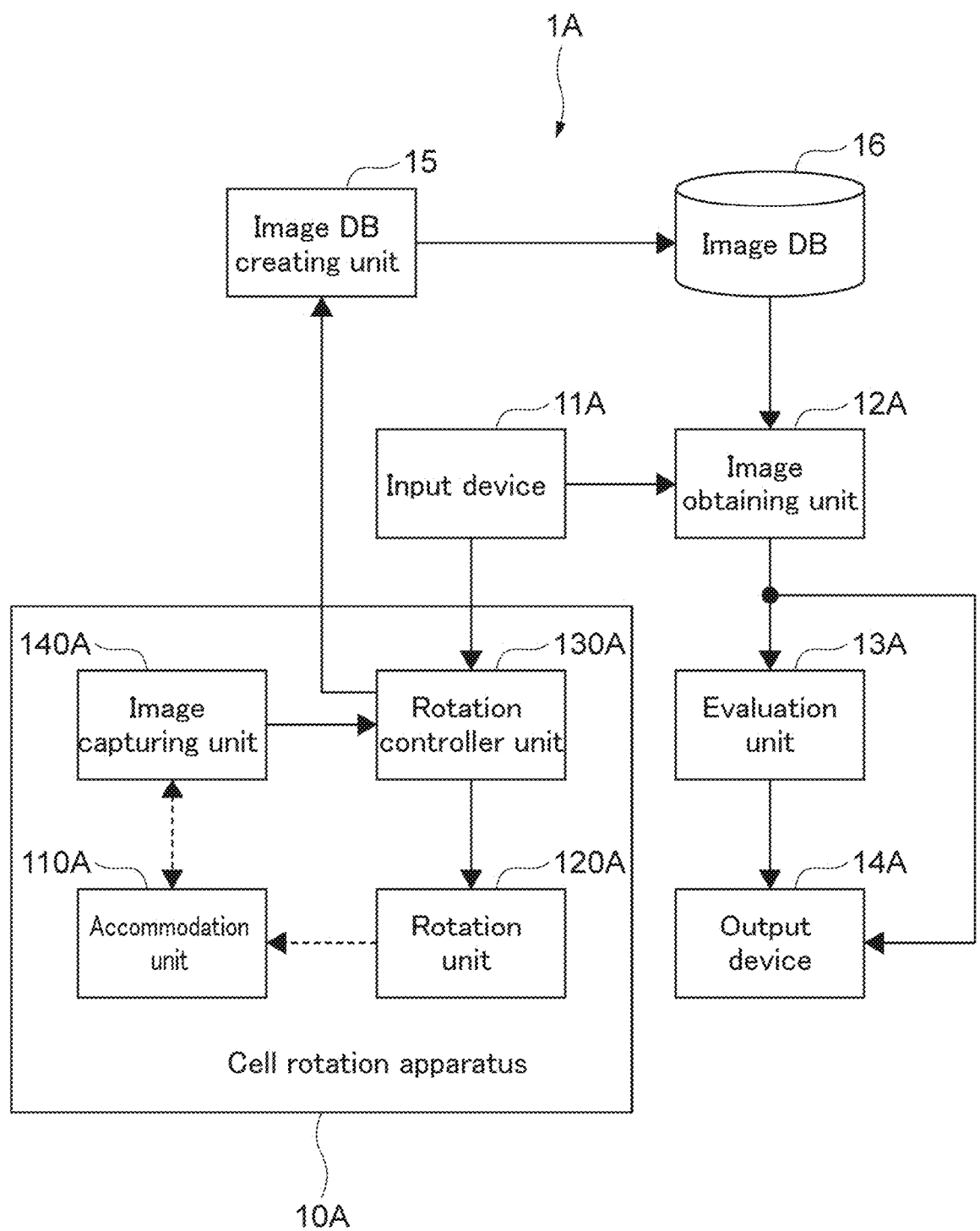
FIG. 9 A block diagram showing a configuration of a cell evaluation apparatus (information processing apparatus) of a second embodiment.

FIG. 9 is a block diagram showing a configuration of a cell evaluation apparatus (information processing apparatus) of a second embodiment.

The cell evaluation apparatus 1A includes the cell rotation apparatus 10A (apparatus), the input device 11A, the image database (DB) creating unit 15, the image database (DB) 16, the image obtaining unit 12A, the evaluation unit 13A, and the output device 14A.

A CPU loads a program recorded in a ROM, which is an example of a non-transitory computer readable recording medium, in a RAM and executes the program to thereby realize at least the image obtaining unit 12A and the evaluation unit 13A of the cell evaluation apparatus 1A, the rotation controller unit 130A of the cell rotation apparatus 10, and the image DB creating unit 15. The image DB 16 is recorded in a nonvolatile recording medium.

The cell rotation apparatus 10A and the input device 11A are similar to the cell rotation apparatus 10 and the input device 11 of the first embodiment. Note that, in the cell rotation apparatus 10A, the rotation controller unit 130A calculates position information of the cell C in three-axis directions on the basis of a rotation direction and a rotation amount input from the input device 11A. For example, the rotation controller unit 130A extracts an interest point in the image of the cell C before rotation and an interest point in the image of the cell C after rotation (the respective interest points are the same positions of the cell C) obtained from the image capturing unit 140A. The rotation controller unit 130A compares the interest point in the image of the cell C before rotation with the interest point in the image of the cell C after rotation, and calculates a rotation direction and a rotation amount of the interest point. The rotation controller unit 130A calculates position information of the cell C in the three-axis directions on the basis of the calculated rotation direction and the calculated rotation amount of the interest point. The rotation controller unit 130A supplies the calculated position information (rotation information) of the cell C in the three-axis directions to the image DB creating unit 15, and the image capturing unit 140A supplies the image of the cell C to the image DB creating unit 15, in synchronization with each other. The "position information of the cell C in the three-axis directions" calculated by the rotation controller unit 130A means not relative position information with reference to the posture of the cell C before rotation but absolute position information (coordinate information, etc.).

The image DB creating unit 15 obtains an image of the cell C and position information of the cell C in the three-axis directions corresponding to the image from the rotation controller unit 130A. The image DB creating unit 15 stores the obtained position information of the cell C in the three-axis directions and the obtained image of the cell to thereby structure the image DB 16 for realizing three-dimensional images.

The image obtaining unit 12A reads, from the image DB 16, the image of the cell C corresponding to a rotation direction and a rotation amount in the three-axis directions input from the input device 11A (or may be an apparatus different from the input device 11A that inputs a rotation direction and a rotation amount in the rotation controller unit 130A). Alternatively, if an image of the cell C corresponding to a rotation direction and a rotation amount in the three-axis directions input from the input device 11A is not stored in the image DB 16, the image obtaining unit 12A may read a plurality of images from the image DB 16, and combine the plurality of read images to thereby generate an image of the cell C corresponding to the input rotation direction and the input rotation amount.

The evaluation unit 13A evaluates the cell on the basis of the images of the cell obtained by the image obtaining unit 12A.

The output device 14A as a display device displays the images of the cell C obtained (read or combined) by the image obtaining unit 12A in real time. The output device 14A further outputs evaluation results of the cell C by the evaluation unit 13A with images, sounds, and the like.

3. Operation of Cell Evaluation Apparatus

Figure 10:
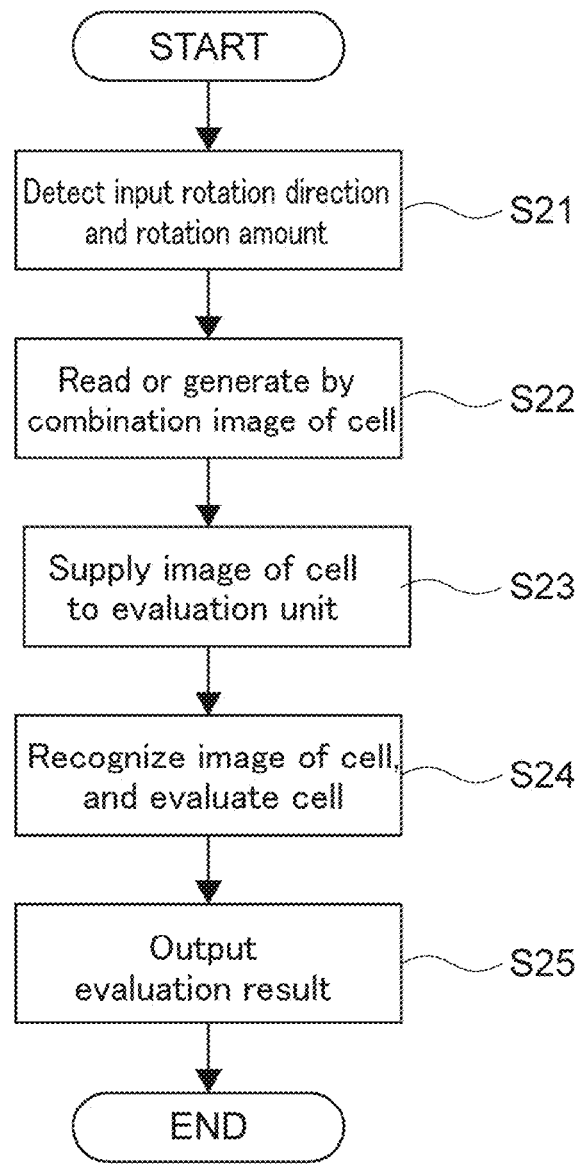
FIG. 10 A flowchart showing an operation of the cell evaluation apparatus.

FIG. 10 is a flowchart showing an operation of the cell evaluation apparatus.

The image DB creating unit 15 stores images of the cell C and position information of the cell C in the three-axis directions obtained from the rotation controller unit 130A to thereby structure the image DB 16 for realizing three-dimensional images. The operation after that will be described.

Before the operation, the image obtaining unit 12A obtains an image of the cell C from the image DB 16 when a certain information is input from the input device 11A as a trigger, for example, and outputs the obtained image to the output device 14A (display device). The image of the cell C is displayed on the output device 14A (display device). When a user is observing the image of the cell C displayed on the output device 14A (display device), the user wishes to watch the cell C in another direction. Then the user operates the input device 11A, and inputs a rotation direction (direction including components of the three axes) and a rotation amount for rotating the cell C.

The image obtaining unit 12A detects the rotation direction (direction including components of three axes) and the rotation amount input from the input device 11A (Step S21). The image obtaining unit 12A reads, from the image DB 16, the image of the cell C corresponding to the rotation direction and the rotation amount input from the input device 11A. Alternatively, if an image of the cell C corresponding to a rotation direction and a rotation amount in the three-axis directions input from the input device 11A is not stored in the image DB 16, the image obtaining unit 12A may read a plurality of images from the image DB 16, and combine the plurality of read images to thereby generate an image of the cell C corresponding to the input rotation direction and the input rotation amount (Step S22). Specifically, the image obtaining unit 12A calculates position information in the three-axis directions of the cell C, which is rotated in the rotation direction and by the rotation amount input from the input device 11A, with reference to the position information of the cell C in the three-axis directions of the image displayed on the output device 14A (display device). The image obtaining unit 12A determines whether an image of the cell C corresponding to the calculated position information in the three-axis directions is stored in the image DB 16. If it is determined that an image is stored, the image obtaining unit 12A reads the image of the cell C corresponding to the calculated position information in the three-axis directions from the image DB 16. If it is determined that an image is not stored, the image obtaining unit 12A reads a plurality of (at least two) images of the cell C corresponding to position information relatively closer to the calculated position information in the three-axis directions from the image DB 16. The image obtaining unit 12A combines the plurality of read images to thereby generate an image of the cell C corresponding to the calculated position information in the three-axis directions.

After the image obtaining unit 12A reads or generates by combination an image of the cell C corresponding to the rotation direction and the rotation amount input from the input device 11A, then the image obtaining unit 12A supplies the read or generated image of the cell C to the evaluation unit 13A (Step S23). The evaluation unit 13A recognizes the obtained image of the cell C by image processing, and evaluates the quality of the cell C with reference to a known database (Step S24). The evaluation unit 13A causes the output device 14A to output the evaluation result by using a predetermined output method (display image or output sound) (Step S25). As a result, a user recognizes the evaluation result of the quality of the cell C output from the output device 14A.

4. Conclusion

According to the present embodiment, since images of a cell rotated by using the cell rotation apparatus 10A are stored in the database, it is possible to three-dimensionally observe and evaluate the cell C afterward. For example, if a cell is a zygote or an embryo, by storing images before the progress of cell division in the database, it is possible to display a past image and the present cell in the accommodation unit 110A simultaneously, and to three-dimensionally compare and observe them simultaneously (in order to realize that, similar to those of FIG. 1, the image obtaining unit 12A obtains images from the image capturing unit 140A of FIG. 9. Not shown).

Further, according to the present embodiment, images of a cell actually rotated by using the cell rotation apparatus 10A are stored in the database. To the contrary, according to a conceivable method, a plurality of image pickup apparatuses obtain images (stereo images) of a cell while the optical distance of the cell is being changed without rotating the cell actually, the images are combined to generate a three-dimensional image, and the three-dimensional image is stored in a database. However, according to this method, since it is necessary to provide a plurality of image pickup apparatuses, the equipment may be complex and the cost may be high. In addition, a three-dimensional image is merely a combination image, and a perfectly-accurate image may not be generated. To the contrary, according to the present embodiment, images of a cell actually rotated by using the cell rotation apparatus 10A are stored in the database. Therefore it is possible to store accurate images as three-dimensional images. In addition, it is only necessary to provide one image pickup apparatus. So the equipment may be simple and the cost may be lower.

5. Modification Examples

According to the present embodiment, as described above, the cell evaluation apparatus 1A is a single apparatus, but not limited to this. For example, the cell evaluation apparatus may include a first apparatus and a second apparatus capable of sending and receiving information via a network or not via a network (not shown). The first apparatus includes the cell rotation apparatus 10A, a first input device 11A, the image DB creating unit 15, and the image DB 16. The second apparatus includes a second input device 11A, the image obtaining unit 12A, the evaluation unit 13A, and the output device 14A. The first apparatus stores images of a cell rotated by the cell rotation apparatus 10A in the image DB 16. Further, the second apparatus obtains images of the cell stored in the image DB 16 of the first apparatus, combines the images as necessary, and outputs a combination image to the output device 14A. The second apparatus may be realized by using a general-purpose personal computer.

Alternatively, for example, the cell evaluation apparatus may include a first apparatus, a second apparatus, and a third apparatus capable of sending and receiving information via a network or not via a network (not shown). The first apparatus includes the cell rotation apparatus 10A, a first input device 11A, and the image DB creating unit 15. The third apparatus includes the image DB 16. The second apparatus includes a second input device 11A, the image obtaining unit 12A, the evaluation unit 13A, and the output device 14A. The first apparatus stores images of a cell rotated by the cell rotation apparatus 10A in the image DB 16 of the third apparatus. Further, the second apparatus obtains images of the cell stored in the image DB 16 of the third apparatus, combines the images as necessary, and outputs a combination image to the output device 14A. The second apparatus may be realized by using a general-purpose personal computer, in this case also. Typically, the first apparatus, the second apparatus, and the third apparatus are connected to a network such as a LAN (Local Area Network) and the Internet. In this case, the third apparatus functions as a so-called server apparatus.

III. Notes

Embodiments and modification examples of the present technology have been described above. The present technology is not limited only to the aforementioned embodiments. The present technology may be variously modified within a scope of the gist of the present technology, as a matter of course.

Note that the present technology may employ the following configurations.

(1) An apparatus, including:
an accommodation unit capable of accommodating a cell and liquid; and
a rotation unit that produces a flow in the liquid in the accommodation unit to rotate the cell.

(2) The apparatus according to (1), in which
the rotation unit includes a first output port that produces a flow of the liquid in contact with a first portion in a first direction to rotate the cell around one axis, the first portion being a part of a surface of the cell.

(3) The apparatus according to (2), in which
the rotation unit further includes a second output port that produces a flow of the liquid in contact with a second portion in a second direction to prevent the cell rotating around the one axis from flowing in the first direction and to rotate the cell around the one axis, the second portion being another part of the surface of the cell, the second direction including a component of a direction opposite to the first direction.

(4) The apparatus according to any one of (1) to (3), further including:
a rotation controller unit that
detects a rotation amount input from an input device, and
controls the flow of the liquid produced by each of the output ports on the basis of the input rotation amount to control a rotation amount of the cell.

(5) The apparatus according to (3) or (4), in which
the rotation unit includes two or more pairs of the first output port and the second output port, and
the pairs are arranged such that the pairs are capable of rotating the cell around an axis including components of two orthogonal axes.

(6) The apparatus according to any one of (3) to (5), in which
the rotation unit includes three or more pairs of the first output port and the second output port, and the pairs are arranged such that the pairs are capable of rotating the cell around an axis including components of three orthogonal axes.

(7) The apparatus according to any one of (4) to (6), in which the rotation controller unit
  detects a rotation direction and a rotation amount input from the input device, and
  controls the flow of the liquid produced by each of the output ports on the basis of the input rotation direction and the input rotation amount to control the rotation direction and the rotation amount of the cell.

(8) The apparatus according to any one of (4) to (7), further including:
  an image capturing unit that captures an image of the cell in the accommodation unit to obtain an image of the cell, in which
  the rotation controller unit
  calculates an actual rotation direction and an actual rotation amount of the cell on the basis of an image of the cell before rotation and an image of the cell after rotation captured by the image capturing unit, and
  controls the flow of the liquid produced by each of the output ports on the basis of the actual rotation direction and the actual rotation amount calculated on the basis of the images of the cell to attain the input rotation direction and the input rotation amount.

(9) The apparatus according to any one of (2) to (8), in which
  each of the output ports injects fluid into the liquid in the accommodation unit to produce the flow of the liquid in the accommodation unit.

(10) The apparatus according to any one of (2) to (8), in which
  each of the output ports vibrates the liquid in the accommodation unit to produce the flow of the liquid in the accommodation unit.

(11) An information processing apparatus, including:
  an image obtaining unit that obtains an image of a cell corresponding to a rotation direction and a rotation amount input from an input device; and
  an evaluation unit that evaluates the cell on the basis of the obtained image of the cell, in which
  the image obtaining unit obtains, as the image of the cell, an image based on an image of the cell obtained by an image capturing unit of an apparatus,
    the apparatus including
    an accommodation unit capable of accommodating the cell and liquid,
    a rotation unit that produces a flow in the liquid in the accommodation unit to rotate the cell,
    a rotation controller unit that controls the rotation unit to control the rotation direction and the rotation amount of the cell, and
    the image capturing unit that captures an image of the cell in the accommodation unit to obtain the image of the cell.

(12) The information processing apparatus according to (11), in which
  the rotation controller unit
  detects the rotation direction and the rotation amount input from the input device, and
  controls the rotation unit on the basis of the input rotation direction and the input rotation amount to control the rotation direction and the rotation amount of the cell,
  the image capturing unit obtains an image of the cell whose rotation direction and rotation amount are controlled on the basis of the input rotation direction and the input rotation amount, and the image obtaining unit obtains the image of the cell from the image capturing unit.

(13) The information processing apparatus according to (11) or (12), in which
  the image obtaining unit
  detects the rotation direction and the rotation amount input from the input device, and
  reads an image of the cell corresponding to the input rotation direction and the input rotation amount from a storage device that stores images of the cell obtained by the image capturing unit and rotation information about rotation directions and rotation amounts of the cell in association with each other, or
  reads a plurality of images from the storage device, combines the plurality of read images, and generates an image of the cell corresponding to the input rotation direction and the input rotation amount.

(14) A program, that causes an information processing apparatus to operate as
  an image obtaining unit that obtains an image of a cell corresponding to a rotation direction and a rotation amount input from an input device; and
  an evaluation unit that evaluates the cell on the basis of the obtained image of the cell, in which
  the image obtaining unit obtains, as the image of the cell, an image based on an image of the cell obtained by an image capturing unit of an apparatus,
    the apparatus including
    an accommodation unit capable of accommodating the cell and liquid,
    a rotation unit that produces a flow in the liquid in the accommodation unit to rotate the cell, and
    the image capturing unit that captures an image of the cell in the accommodation unit to obtain the image of the cell.

(15) An information processing method, including:
  by an image obtaining unit, obtaining an image of a cell corresponding to a rotation direction and a rotation amount input from an input device; and
  by an evaluation unit, evaluating the cell on the basis of the obtained image of the cell, in which
  the image obtaining unit obtains, as the image of the cell, an image based on an image of the cell obtained by an image capturing unit of an apparatus,
    the apparatus including
    an accommodation unit capable of accommodating the cell and liquid,
    a rotation unit that produces a flow in the liquid in the accommodation unit to rotate the cell, and
    the image capturing unit that captures an image of the cell in the accommodation unit to obtain the image of the cell.

REFERENCE SIGNS LIST 1, 1A cell evaluation apparatus
10, 10A cell rotation apparatus
11, 11A input device
12, 12A image obtaining unit
13, 13A evaluation unit
14, 14A output device
15 image DB creating unit
16 image DB
110, 110A accommodation unit
120, 120A rotation unit
130, 130A rotation controller unit
140, 140A image capturing unit

The invention claimed is:

1. An apparatus, comprising:
an accommodation unit capable of accommodating a cell and liquid;
a rotation unit that produces a flow in the liquid in the accommodation unit to rotate the cell; and
a rotation controller unit that controls the flow of the liquid on a basis of an actual rotation direction and an actual rotation amount both calculated on a basis of an image of the cell before rotation and an image of the cell after rotation.

2. The apparatus according to claim 1, wherein
the rotation unit includes a first output port that produces a flow of the liquid in contact with a first portion in a first direction to rotate the cell around one axis, the first portion being a part of a surface of the cell.

3. The apparatus according to claim 2, wherein
the rotation unit further includes a second output port that produces a flow of the liquid in contact with a second portion in a second direction to prevent the cell rotating around the one axis from flowing in the first direction and to rotate the cell around the one axis, the second portion being another part of the surface of the cell, the second direction including a component of a direction opposite to the first direction.

4. The apparatus according to claim 3, wherein:
the rotation controller unit
detects a rotation amount input from an input device, and
controls the flow of the liquid produced by each of the output ports on a basis of the input rotation amount to control a rotation amount of the cell.

5. The apparatus according to claim 4, wherein
the rotation unit includes two or more pairs of the first output port and the second output port, and
the pairs are arranged such that the pairs are capable of rotating the cell around an axis including components of two orthogonal axes.

6. The apparatus according to claim 5, wherein
the rotation unit includes three or more pairs of the first output port and the second output port, and
the pairs are arranged such that the pairs are capable of rotating the cell around an axis including components of three orthogonal axes.

7. The apparatus according to claim 6, wherein
the rotation controller unit
detects a rotation direction and a rotation amount input from the input device, and
controls the flow of the liquid produced by each of the output ports on a basis of the input rotation direction and the input rotation amount to control the rotation direction and the rotation amount of the cell.

8. The apparatus according to claim 7, further comprising:
an image capturing unit that captures the images of the cell in the accommodation unit to obtain the images of the cell, wherein
the rotation controller unit
calculates the actual rotation direction and the actual rotation amount of the cell on the basis of the image of the cell before rotation and the image of the cell after rotation captured by the image capturing unit, and
wherein the actual rotation direction and the actual rotation amount are calculated to attain the input rotation direction and the input rotation amount.

9. The apparatus according to claim 3, wherein
each of the output ports injects fluid into the liquid in the accommodation unit to produce the flow of the liquid in the accommodation unit.

10. The apparatus according to claim 3, wherein
each of the output ports vibrates the liquid in the accommodation unit to produce the flow of the liquid in the accommodation unit.

11. An information processing apparatus, comprising:
an image obtaining unit that obtains at least one image of a cell corresponding to a rotation direction and a rotation amount input from an input device; and
an evaluation unit that evaluates the cell on a basis of the obtained at least one image of the cell, wherein
the obtained at least one image of the cell is based on one or more images of the cell captured by an image capturing unit of an apparatus,
the apparatus including
an accommodation unit capable of accommodating the cell and liquid,
a rotation unit that produces a flow in the liquid in the accommodation unit to rotate the cell,
a rotation controller unit that, on a basis of an actual rotation direction and an actual rotation amount both calculated on a basis of an image of the cell before rotation and an image of the cell after rotation, controls the rotation unit to control the rotation direction and the rotation amount of the cell, and
the image capturing unit that captures the one or more images of the cell in the accommodation unit.

12. The information processing apparatus according to claim 11, wherein
the rotation controller unit
detects the rotation direction and the rotation amount input from the input device, and
controls the rotation unit on a basis of the input rotation direction and the input rotation amount to control the rotation direction and the rotation amount of the cell,
the image capturing unit obtains an image of the cell whose rotation direction and rotation amount are controlled on a basis of the input rotation direction and the input rotation amount, and
the image obtaining unit obtains the image of the cell from the image capturing unit.

13. The information processing apparatus according to claim 11, wherein
the image obtaining unit
detects the rotation direction and the rotation amount input from the input device, and
reads an image of the cell corresponding to the input rotation direction and the input rotation amount from a storage device that stores images of the cell obtained by the image capturing unit and rotation information about rotation directions and rotation amounts of the cell in association with each other, or
reads a plurality of images from the storage device, combines the plurality of read images, and generates an image of the cell corresponding to the input rotation direction and the input rotation amount.

14. At least one non-transitory computer-readable storage medium encoded with executable instructions that, when executed by at least one processor, cause the at least one processor to function as:
an image obtaining unit that obtains at least one image of a cell corresponding to a rotation direction and a rotation amount input from an input device; and an evaluation unit that evaluates the cell on a basis of the obtained at least one image of the cell, wherein the obtained at least one image of the cell is based on one or more images of the cell captured by an image capturing unit of an apparatus, the apparatus including an accommodation unit capable of accommodating the cell and liquid, a rotation unit that produces a flow in the liquid in the accommodation unit to rotate the cell, a rotation controller unit that controls the flow of the liquid on a basis of an actual rotation direction and an actual rotation amount both calculated on a basis of an image of the cell before rotation and an image of the cell after rotation, and the image capturing unit that captures the one or more images of the cell in the accommodation unit.

15. An information processing method, comprising:

by an image obtaining unit, obtaining at least one image of a cell corresponding to a rotation direction and a rotation amount input from an input device; and by an evaluation unit, evaluating the cell on a basis of the obtained at least one image of the cell, wherein the obtained at least one image of the cell is based on one or more images of the cell captured by an image capturing unit of an apparatus, the apparatus including an accommodation unit capable of accommodating the cell and liquid, a rotation unit that produces a flow in the liquid in the accommodation unit to rotate the cell, a rotation controller unit that controls the flow of the liquid on a basis of an actual rotation direction and an actual rotation amount both calculated on a basis of an image of the cell before rotation and an image of the cell after rotation, and the image capturing unit that captures the one or more images of the cell in the accommodation unit.

* * * * *